US012653925B2

(12) United States Patent
Du

(10) Patent No.: US 12,653,925 B2
(45) Date of Patent: Jun. 16, 2026

(54) METHOD FOR PREPARING BIONIC COLLAGEN AQUEOUS SOLUTION AND USE METHOD THEREOF

(71) Applicant: Mingchun Du, Chengdu (CN)

(72) Inventor: Mingchun Du, Chengdu (CN)

( * ) Notice: Subject to any disclaimer, the term of this patent is extended or adjusted under 35 U.S.C. 154(b) by 644 days.

(21) Appl. No.: 18/162,305

(22) Filed: Jan. 31, 2023

(65) Prior Publication Data

US 2023/0173137 A1     Jun. 8, 2023

Related U.S. Application Data

(63) Continuation of application No. PCT/CN2021/125224, filed on Oct. 21, 2021.

(30) Foreign Application Priority Data

Oct. 26, 2020     (CN) .......................... 202011152941.9

(51) Int. Cl.
| | |
|---|---|
| *A61L 26/00* | (2006.01) |
| *A61L 27/24* | (2006.01) |
| *A61L 27/36* | (2006.01) |
| *A61L 27/52* | (2006.01) |

(52) U.S. Cl.
CPC ......... *A61L 26/0033* (2013.01); *A61L 26/008* (2013.01); *A61L 27/24* (2013.01); *A61L 27/52* (2013.01); *A61L 2400/06* (2013.01); *A61L 2430/34* (2013.01)

(58) Field of Classification Search
CPC .. A61L 26/0033; A61L 26/0038; A61L 27/60; A61L 27/36; A61L 27/362; A61L 2400/06; A61K 47/6955; A61K 47/6903
See application file for complete search history.

(56) References Cited

FOREIGN PATENT DOCUMENTS

| | | |
|---|---|---|
| CN | 101934092 A | 1/2011 |
| CN | 104399120 A | 3/2015 |
| CN | 105641740 A | 6/2016 |
| CN | 106913912 A | 7/2017 |
| CN | 107308494 A | 11/2017 |
| CN | 108434514 A | 8/2018 |
| CN | 112354013 A | 2/2021 |
| CN | 112402289 A | 2/2021 |
| JP | 2004515451 A | 5/2004 |
| JP | 2010528046 A | 8/2010 |
| JP | 2014103985 A | 6/2014 |
| JP | 2016077410 A | 5/2016 |
| JP | 2017095400 A | 6/2017 |

OTHER PUBLICATIONS

He et al., Polymers, 2021, 13, 2299, pp. 1-26.*
Extended European Search Report issued on Nov. 22, 2023 in corresponding PCT Application No. PCT/CN2021/125224, 8 pages.
First Office Action issued on Dec. 26, 2023 in correspond Japan Patent Application No. 2023-504754, 10 pages with English translation.
Nippon-Ham Central Laboratory "Collagen". Retrievd from https://www.rdc.nipponham.co.jp/pdf/medcollagen2.pdf on Dec. 18, 2023, 4 pages with English translation.

* cited by examiner

*Primary Examiner* — Maryam Monshipouri
(74) *Attorney, Agent, or Firm* — MUNCY, GEISSLER, OLDS & LOWE, P.C.

(57)     ABSTRACT

A bionic collagen aqueous solution, and a preparation method therefor and a use method thereof. By adding simulated body fluid components, the ion components and ion strength of the collagen aqueous solution are regulated, the pH value is regulated, and a tissue microenvironment is simulated. By adding connecting molecules, the binding of collagen molecules to tissues is improved, and the biocompatibility of the collagen aqueous solution is enhanced. The concentration of the collagen aqueous solution is greater than 0.1 wt. % and less than or equal to 10 wt. %. The collagen aqueous solution is used to cover the surface of the skin in the form of a dressing, can also be applied to the body in an injected manner. The bionic collagen aqueous solution simulates some characteristics of pre-repaired tissue, has a good biocompatibility, and delays the degradation of collagen molecules during use, which is beneficial for tissue repair and regeneration.

9 Claims, 1 Drawing Sheet

METHOD FOR PREPARING BIONIC COLLAGEN AQUEOUS SOLUTION AND USE METHOD THEREOF

CROSS REFERENCE TO RELATED APPLICATIONS

This application is a Continuation of co-pending Application PCT/CN2021/125224, filed on Oct. 21, 2021, for which priority is claimed under 35 U.S.C. § 120; which claims priority of Application No. 202011152941.9 filed in China on Oct. 26, 2020 under 35 U.S.C. § 119, the entire contents of all of which are hereby incorporated by reference.

TECHNICAL FIELD

The present invention relates to a biological material and a preparation method therefor and a use method thereof, and particularly to a preparation method for and a use method of a bionic collagen aqueous solution.

BACKGROUND

Collagen is the main structural protein of connective tissue, which is widely distributed in tissues and organs such as human bones, skin, blood vessels, ligaments, cartilage, muscles and tendons, accounting for 25% to 30% of the total protein in animals. So far, more than 20 kinds of collagen have been identified, among which type I collagen has the highest content of about 90%. In the skin, collagen is distributed in the dermis, and its content is about 70%, mainly of types I (85%), III and V. However, due to the influence of ion components, ion strength, pH value, and other factors, the biocompatibility and degradability of collagen in the tissue repair process still need to be improved.

For example, collagen materials are easily degraded in the body, which affects the skin repair effect. In order to delay the degradation of collagen in the body, chemical cross-linking agents such as glutaraldehyde, hexamethylene diisocyanate, carbodiimide, and diphenyl phosphoryl azide, are often used to cross-link the collagen aqueous solution. Among them, glutaraldehyde is the most widely used reagent. However, numerous experiments have demonstrated that glutaraldehyde can react rapidly with collagen molecules to provide effective cross-linking, but glutaraldehyde is cytotoxic and it is difficult to control its dosage. In addition, as the degree of cross-linking increases, the water absorption capacity and swelling of the collagen materials will decrease, which also affects the effectiveness of the collagen materials.

SUMMARY OF THE INVENTION

In response to at least one aspect of the above problems in the use of a collagen aqueous solution, a bionic collagen aqueous solution is developed in the present invention from the viewpoint of bionics: (1) by employing high-concentration collagen to simulate the composition of pre-repaired tissues, and adding simulated body fluid components to regulate the solution environment (e.g., ion components, ion strength, etc.), the pH of the solution can be further regulated so as to form a stable and flowable collagen aqueous solution, thereby simulating the microenvironment of pre-repaired tissues; (2) by adding connecting molecules, which facilitates the binding of the collagen aqueous solution to surrounding tissues during use, the biocompatibility of the collagen aqueous solution can be enhanced, and the degradation of the collagen molecules can be delayed at the same time. The developed high-concentration bionic collagen aqueous solution can be used to cover the surface of a pre-repaired wound in the form of a dressing or applied to the body in an injected manner, so as to promote tissue repair and regeneration.

The present invention provides a bionic collagen aqueous solution and a preparation method therefor and a use method thereof.

According to one aspect of the present invention, there is provided a method for preparing a bionic collagen aqueous solution, including the following steps in order:

(1) placing solid collagen materials in water, then adding an acidic solution while stirring to dissolve the solid collagen materials to form a homogeneous aqueous solution, the resulting collagen aqueous solution has a concentration of greater than 0.1 wt. % of and less than or equal to 10 wt. %;

(2) adding the collagen aqueous solution obtained from step (1) into simulated body fluid components slowly while stirring at low temperature for fully dissolution;

(3) adjusting the collagen aqueous solution obtained from step (2) with an alkaline solution or an acidic solution at low temperature to a pH value of greater than or equal to 6 and less than or equal to 8, to form a homogeneous solution;

(4) adding a connecting molecule solution into the collagen aqueous solution obtained from step (3) and stirring uniformly at low temperature to complete the preparation, after then storing the bionic collagen aqueous solution at low temperature.

In an embodiment of the present invention, the low temperature in step (2), step (3), and step (4) is in a range of greater than or equal to 0° C. and less than or equal to 5° C.; in the step (3), the collagen aqueous solution is adjusted with the alkaline solution or acidic solution to a pH value of greater than or equal to 7.0 and less than or equal to 7.5; in the step (4), after adding the connecting molecule solution and stirring uniformly, the resulting bionic collagen solution is stored at low temperature for a period of greater than or equal to 0 min and less than or equal to 30 min.

In an embodiment of the present invention, the acidic solution in step (1) and step (3) is at least one of hydrochloric acid, nitric acid, sulfuric acid, phosphoric acid, tartaric acid, citric acid, oxalic acid, acetic acid, and formic acid; the alkaline solution in step (3) includes at least one of triethylamine, tetramethyl ethylenediamine, pyridine, piperidine, sodium hydroxide, potassium hydroxide, calcium hydroxide, magnesium hydroxide, ammonia, disodium hydrogen phosphate, and sodium bicarbonate; the concentration of the acidic solution or the alkaline solution is greater than or equal to 0.01 M and less than 10 M.

In an embodiment of the present invention, the acidic solution in step (1) is added in order to fully dissolve the solid collagen materials and it is added in a small amount without significantly changing the concentration of collagen therein, provided that the collagen is dissolved to form a homogeneous solution.

In an embodiment of the present invention, the alkaline solution or acidic solution in step (3) is added in order to adjust the pH of the collagen aqueous solution and it is added in a small amount without significantly changing the concentration of collagen therein, provided that the aqueous solution reaches a predefined pH value and forms a homogeneous solution.

In an embodiment of the present invention, the simulated body fluid components include a combination of one or two or more of $Na^+$, $K^+$, $Mg^{2+}$, $Ca^{2+}$, $Cl^-$, $HCO_3^-$, $HPO_4^{2-}$, $SO_4^{2-}$, $CO_3^{2-}$, $PO_4^{3-}$, and $H_2PO_4^-$. The simulated body fluid components are added in order to adapt the ionic environment of the collagen aqueous solution to the microenvironment of the pre-repaired tissues, and they are added in small amounts without significantly changing the concentration of collagen therein. In the bionic collagen aqueous solution, the final ionic concentration of various ions is in a range of 0.1 to 500 mM, and the final total ionic concentration is in a range of 0.1 to 1000 mM.

In an embodiment of the present invention, the connecting molecules are a mixture of one or two or more of isothiocyanate, isocyanate, acyl azide, N-hydroxysuccinimide ester (NHS ester), sulfonyl chloride, aldehyde, epoxide, aryl halide, imide ester, carbodiimide, acid anhydride, fluorophenyl ester, procyanidine, and genipin. The connecting molecules are added in order to enhance the binding of the collagen molecules to pre-repaired tissues, without significantly changing the concentration of collagen therein. The final concentration of the connecting molecules in the bionic collagen aqueous solution is greater than or equal to 0.0001 wt. % of and less than or equal to 10 wt. %.

In an embodiment of the present invention, the final concentration of the connecting molecules in the bionic collagen aqueous solution is greater than or equal to 0.0001 wt. % of and less than or equal to 1 wt. %.

In an embodiment of the present invention, the final concentration of the connecting molecules in the bionic collagen aqueous solution is greater than or equal to 0.0001 wt. % of and less than or equal to 0.1 wt. %.

In an embodiment of the present invention, the final concentration of the connecting molecules in the bionic collagen aqueous solution is greater than or equal to 0.001 wt. % of and less than or equal to 0.01 wt. %.

According to another aspect of the present invention, there is provided a method of using the bionic collagen aqueous solution prepared by the method for preparing a bionic collagen aqueous solution as described in any one of the foregoing embodiments.

In an embodiment of the present invention, the bionic collagen aqueous solution is used to cover the surface of a pre-repaired wound in the form of a dressing or applied to the body in an injected manner within 30 min after its preparation.

In the method for preparing a bionic collagen aqueous solution according to embodiments of the present invention, due to the addition of connecting molecules, there is a possibility of reaction between the collagen molecules and the connecting molecules before the bionic collagen aqueous solution is used, thus affecting the fluidity of the collagen solution, which is beneficial for its use, especially for its application to the body in an injected manner. In addition, high-concentration collagen is also prone to form non-fluid hydrogel structure under neutral conditions. Therefore, in the preparation method of the embodiments of the present invention, after the addition of connecting molecules, the storage time of the bionic collagen aqueous solution is greater than or equal to 0 min and less than or equal to 30 min, so as not to affect its fluidity and usage effects.

The embodiments of the present invention are solutions proposed from the viewpoint of bionics against the problem of poor biocompatibility in the use of high-concentration collagen solutions. In order to improve the biocompatibility of high-concentration collagen, the following optimizations are mainly made in the present invention: (1) on the basis of the ion components and contents in the pre-repaired tissue body fluid as well as the pH environment, simulated body fluid components are added in the solution to regulate the solution environment (e.g., ion strength, osmotic pressure, etc.), and further regulate the pH value, so that the collagen solution matches the microenvironment of the pre-repaired tissues; (2) connecting molecules are added in the collagen solution of the present invention, which can react with both the collagen molecules in the collagen solution and the collagen components in the pre-repaired tissues, and the reaction is mild, thus promoting the binding of collagen molecules to pre-repaired tissues.

The solution environment in the bionic collagen aqueous solution of the present invention is closer to the microenvironment of pre-repaired tissues, and its biocompatibility is much better than that of a regular collagen solution. Moreover, the addition of connecting molecules can also delay the degradation of collagen molecules, thereby exerting their biological activity and promoting tissue repair and regeneration.

DETAILED DESCRIPTION

Figures 1A, 1B, 1C, 1D, 1E, 1F, 2A, 2B, 2C, 2D, 2E, 2F:
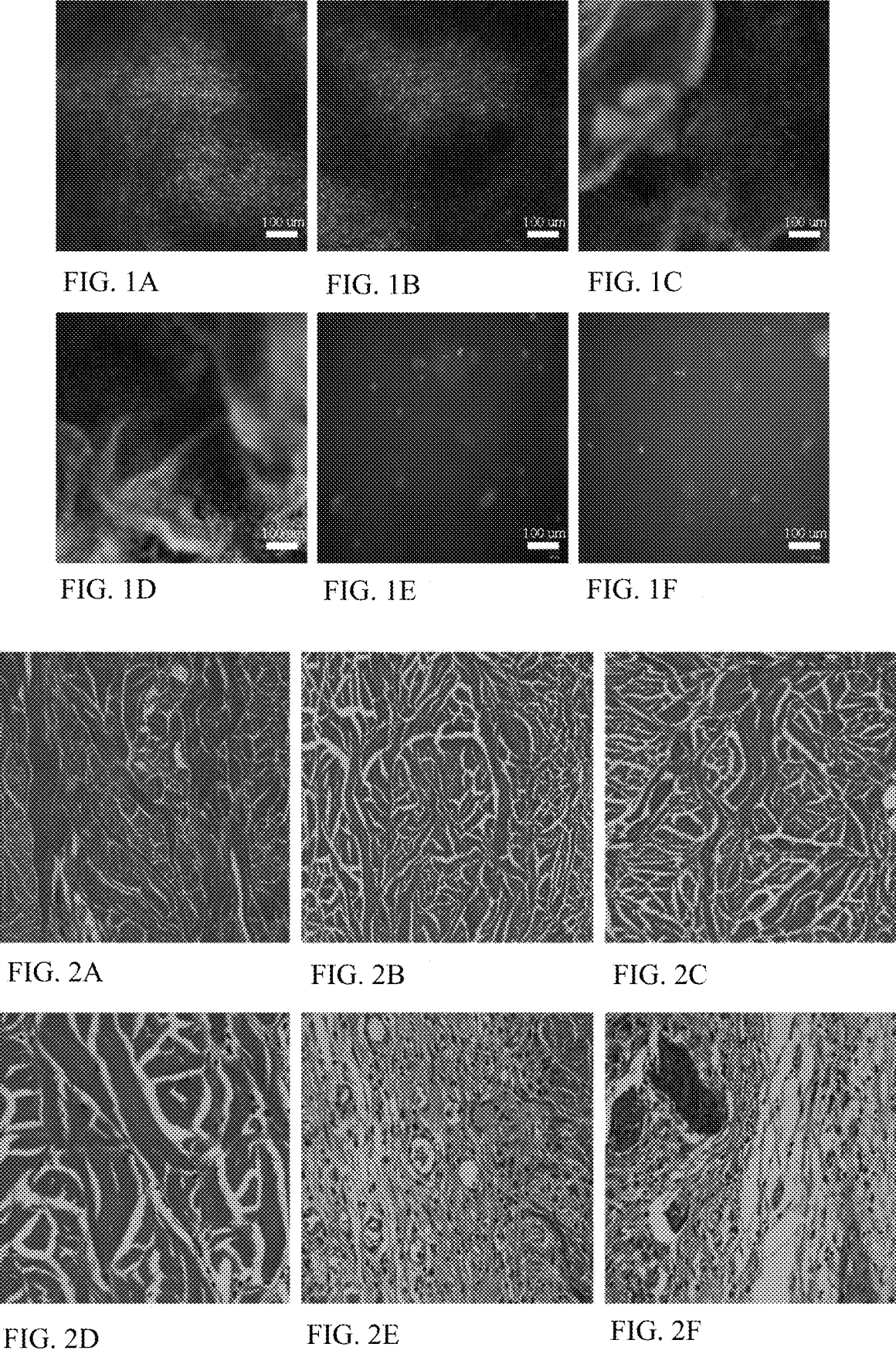
FIGS. 1A-1F are diagrams showing the live/dead cell staining effect profile in the bionic collagen aqueous solution according to an embodiment of the present invention (FIG. 1A represents the sample in Embodiment 1, FIG. 1B represents the sample in Embodiment 2, FIG. 1C represents the sample in Embodiment 3, FIG. 1D represents the sample in Embodiment 4, FIG. 1E represents the sample in Comparative Embodiment 1, and FIG. 1F represents the sample in Comparative Embodiment 2)
FIGS. 2A-2F are diagrams showing the HE staining (Hematoxylin-eosin staining) effect profile of the bionic collagen aqueous solution implanted in rats according to an embodiment of the present invention (FIG. 2A represents the sample in Embodiment 1, FIG. 2B represents the sample in Embodiment 2, FIG. 2C represents the sample in Embodiment 3, FIG. 2D represents the sample in Embodiment 4, FIG. 2E represents the sample in Comparative Embodiment 1, and FIG. 2F represents the sample in Comparative Embodiment 2).

The technical solutions of the present invention will be further specified below through the embodiments and in conjunction with the accompanying drawings. In the specification, the same or like reference numerals indicate the same or like parts. The following description of embodiments of the present invention with reference to the accompanying drawings is intended to explain the general inventive concept of the present invention and should not be construed as a limitation of the present invention.

Embodiment 1

A method for preparing a bionic collagen aqueous solution, including the following steps in order:

(1) placing 2 g of collagen materials into 100 g of deionized water, and adding 0.01 M of acetic acid solution while stirring to dissolve the collagen materials to form a homogeneous aqueous solution;

(2) adding the collagen aqueous solution obtained from step (1) into 1 g of $Na_2HPO_4$ and 0.2 g of $KH_2PO_4$ slowly while stirring at 0° C. for fully dissolution;

(3) adjusting the collagen aqueous solution obtained from step (2) with 0.1 M of NaOH solution or 0.01 M of acetic acid solution at 5° C. to pH 7.4, to form a homogeneous solution;

(4) adding 0.001 wt. % of procyanidine solution and 0.02 wt. % of isocyanate into the collagen aqueous solution obtained from step (3) and stirring uniformly at 2° C.

A method of using a bionic collagen aqueous solution prepared by the preparation method described above, including: covering the bionic collagen aqueous solution in the form of a dressing uniformly over the surface of the burnt skin after 5 min of its formulation.

Embodiment 2

A method for preparing a bionic collagen aqueous solution, including the following steps in order:

(1) placing 5 g of collagen materials into 200 g of deionized water, and adding 0.1 M of hydrochloric acid solution while stirring to dissolve the collagen materials to form a homogeneous aqueous solution;

(2) adding the collagen aqueous solution obtained from step (1) into 1 g of KCl and 3 g of $Na_2HPO_4$ slowly while stirring at 4° C. for fully dissolution;

(3) adjusting the collagen aqueous solution obtained from step (2) with 1 M of KOH solution or 1 M of formic acid solution at 4° C. to pH 6, to form a homogeneous solution;

(4) adding 1 wt. % of glyoxal and 2 wt. % of NHS ester solution into the collagen aqueous solution obtained from step (3) and stirring uniformly at 0° C.

A method of using a bionic collagen aqueous solution prepared by the preparation method described above, including: applying the bionic collagen aqueous solution in an injected manner for soft tissue repair after 0 min of its formulation.

Embodiment 3

A method for preparing a bionic collagen aqueous solution, including the following steps in order:

(1) placing 3 g of collagen materials into 200 g of deionized water, and adding 1 M of tartaric acid solution while stirring to dissolve the collagen materials to form a homogeneous aqueous solution;

(2) adding the collagen aqueous solution obtained from step (1) into 2 g of $NaH_2PO_4$ and 1 g of KCl slowly while stirring at 5° C. for fully dissolution;

(3) adjusting the collagen aqueous solution obtained from step (2) with 2 M of potassium hydroxide solution or 1 M of formic acid solution at 5° C. to pH 8, to form a homogeneous solution;

(4) adding 2 wt. % of isothiocyanate solution into the collagen aqueous solution obtained from step (3) and stirring uniformly at 4° C.

A method of using a bionic collagen aqueous solution prepared by the preparation method described above, including: applying the bionic collagen aqueous solution in an injected manner for soft tissue repair after 30 min of its formulation.

Embodiment 4

A method for preparing a bionic collagen aqueous solution, including the following steps in order:

(1) placing 1 g of collagen materials into 1000 g of deionized water, and adding 0.1 M of oxalic acid solution while stirring to dissolve the collagen materials to form a homogeneous collagen aqueous solution;

(2) adding the collagen aqueous solution obtained from step (1) into 3 g of $K_2SO_4$ and 5 g of $KHCO_3$ slowly while stirring at 3° C. for fully dissolution;

(3) adjusting the collagen aqueous solution with 2 M of aqueous ammonia solution or 5 M of citric acid solution at 0° C. to pH 7.0, to form a homogeneous solution;

(4) adding 10 wt. % of ethylene oxide solution and 0.5 wt. % of genipin solution into the collagen aqueous solution and stirring uniformly at 5° C.

A method of using a bionic collagen aqueous solution prepared by the preparation method described above, including: covering the bionic collagen aqueous solution in the form of a dressing uniformly over the surface of the scalded skin after 15 min of its formulation.

Embodiment 5

Comparative Test on the Effect of the Bionic Collagen Aqueous Solution

I. Preparation of the Control Collagen Aqueous Solution

Comparative embodiment 1: A method for preparing a collagen aqueous solution and a use method thereof, including the following steps in order:

placing 2 g of collagen materials into 200 g of deionized water, and adding 1 M of tartaric acid solution while stirring to dissolve the collagen materials to form a homogeneous aqueous solution;

the collagen aqueous solution prepared above is applied in an injected manner for soft tissue repair.

Comparative embodiment 2: A method for preparing a collagen aqueous solution and a use method thereof, including the following steps in order:

placing 1 g of collagen materials into 1000 g of deionized water, and adding 0.1 M of acetic acid solution while stirring to dissolve the collagen materials to form a homogeneous aqueous solution;

the collagen aqueous solution prepared above is applied in the form of a dressing over the surface of the burnt skin.

II. Comparison of Effect Tests (1) Tests for comparison of three-dimensional culture: collagen aqueous solutions were prepared according to the preparation methods in Embodiments 1-4 and Comparative Embodiments 1-2, from each of which 2 mL was taken and mixed with $7\times10^6$ rat vascular endothelial cells (Shanghai Cell Bank, Chinese Academy of Sciences) at 37° C. to form collagen hydrogel-encapsulated cells for three-dimensional culture experiments. The medium was high glucose DMEM (HyClone) medium containing 10% (v/v %) fetal bovine serum and 1% streptomycin and penicillin, and was replaced once a day. The incubator (STEM 371, Thermo Electron Corporation) was set at 37° C. with humid air containing 5% (v/v %) $CO_2$. After 7 days of culture, the cells in the hydrogel were treated by live/dead cell staining, with the staining solution being 2 mmol/L of calcein-AM (calcein acetoxymethyl ester solution, Sigma) (for staining live cells and emitting green fluorescence) and 2 mmol/L of EthD-1 solution (Ethidium Homodimer 1, Sigma) (for staining dead cells and emitting red fluorescence). The samples were observed on an A1 confocal laser microscope (Nikon), with the wavelength of green excitation light being 488 nm, and the wavelength of red excitation light being 562 nm. The live/dead cell staining profile in the collagen hydrogel was seen in FIG. 1A to FIG. 1F. It can be known from FIG. 1A to FIG. 1F that, since the collagen solutions in Embodiments 1-4 are closer to the in vivo tissue microenvironment, the collagen hydrogels they form are more suitable for cell growth, and the fluorescent signals representing live cells (e.g., green fluorescence signals) are stronger in FIG. 1A to FIG. 1D of the samples in these embodiments, demonstrating that cells can grow properly in these collagen solutions and that the materials are more biocompatible. However, in Comparative Embodiments 1-2, the collagen hydrogels are not suitable for cell growth, and the fluorescent signals representing dead cells (e.g., red fluorescent signals) are stronger in FIG. 1E and FIG. 1F of the samples in the comparative embodiments, demonstrating that cells cannot grow properly in the collagen hydrogels and that the biocompatibility of the materials is poor. Therefore, in the embodiments of the present disclosure, the addition of simulated body fluid components and the regulation of pH are more favorable for cell growth, and the collagen solutions also exhibit better biocompatibility.

(2) Tests for comparison of histocompatibility:

Into the muscles of rats were respectively implanted with the collagen aqueous solutions prepared according to the preparation methods of Embodiments 1-4 and Comparative Embodiments 1-2. The experimental rats were sacrificed one month later, from which the implanted materials were taken out and fixed with 4 wt. % paraformaldehyde fixation solution for HE staining.

The specific steps are as follows:

(1) embedding the sample in a paraffin embedding machine, then slicing it with a slicer, putting the cut slices into a water bath at 60° C., inserting a glass slide carefully into the water close to the slices, transferring the floating paraffin slices onto the glass slide, and picking out the blisters with a needle, if any.

(2) dehydrating the slices with xylene twice, each time for 5 min, rinsing with 100% alcohol, 95% alcohol, 85% alcohol, 70% alcohol, 50% alcohol sequentially, and rinsing with tap water, then staining with hematoxylin for 5 min, and rinsing with tap water again to turn the color blue.

(3) putting the slices into 1% hydrochloric acid ethanol solution to fade for 2-10 seconds, with the color becoming light red, and then rinsing with tap water again to bring the color back to blue.

(4) then putting the slices into 50% alcohol, 70% alcohol, and 80% alcohol and keeping for 5 min respectively, and performing contrast staining with 0.5% eosin alcohol solution for 1-3 min.

(5) washing the slices in 95% alcohol to remove excess red color, then putting them into 100% alcohol for 3-5 min, absorbing excess alcohol with absorbent paper, and putting the slices into xylene I and II for 3-5 min each.

(6) sealing and fixing with neutral balsam.

The HE staining results of different sample are shown in FIG. 2A to FIG. 2F. It can be known from FIG. 2A to FIG. 2F that, since the collagen aqueous solutions in the embodiments (FIGS. 2A to 2D) are closer to the in vivo tissue microenvironment of rats, materials can fuse with the surrounding tissues quickly after implantation, and only a small number of inflammatory cells are found, while a large number of inflammatory cells are found in the comparative embodiments (FIGS. 2E to 2F), showing the poor histocompatibility of the materials. Therefore, in the embodiments of the present disclosure, the addition of simulated body fluid components, the regulation of pH, and the addition of connecting molecules can significantly improve the histocompatibility of the collagen solutions in the body.

It can be known from the above tests that, in the comparison among Embodiments 1-4 and Comparative embodiments 1-2, the collagen materials are dissolved in a strong acid environment in Comparative embodiments 1-2, which is not beneficial for its use and the efficacy of tissue repair; while the use environment of the collagen materials in Embodiments 1-4 can be regulated depending on the changes of the microenvironment in the body, such as pH environment, ion components, ion strength, etc., so that the collagen materials can be used for tissue repair in the body. In addition, due to the addition of connecting molecules, the collagen molecules in the solution can be tightly bound to the surrounding tissues through the connecting molecules, which facilitates the tissue repair effect of the collagen materials.

The foregoing embodiments are only a description of preferred embodiments of the present invention. Without departing from the spirit of the design of the present invention, all kinds of variations and improvements made to the technical solutions of the present invention by those skilled in the art shall fall within the scope of protection defined by the claims of the present invention.

The invention claimed is:

1. A method for preparing a bionic collagen aqueous solution, wherein, comprising the following steps in order:

(1) placing solid animal-derived type I collagen in water, then adding an acidic solution while stirring to dissolve the solid animal-derived type I collagen to form a homogeneous aqueous solution, the resulting collagen aqueous solution has a concentration of greater than 0.1 wt. % of and less than or equal to 10 wt. %;

(2) adding the collagen aqueous solution obtained from step (1) into simulated body fluid components slowly while stirring at a temperature greater than or equal to 0° C. but less than or equal to 5° C. for fully dissolution;

(3) adjusting the collagen aqueous solution obtained from step (2) with an alkaline solution or an acidic solution at a temperature greater than or equal to 0° C. but less than or equal to 5° C. to a pH value of greater than or equal to 6 and less than or equal to 8, to form a homogeneous solution;

(4) adding a connecting molecule solution into the collagen aqueous solution obtained from step (3) and stirring uniformly at a temperature greater than or equal to 0° C. but less than or equal to 5° C. to complete the preparation, after then storing the bionic collagen aqueous solution at a temperature greater than or equal to 0° C. but less than or equal to 5° C.

2. The method for preparing a bionic collagen aqueous solution according to claim 1, wherein, the collagen aqueous solution is adjusted with the alkaline solution or acidic solution to a pH value of greater than or equal to 7.0 and less than or equal to 7.5.

3. The method for preparing a bionic collagen aqueous solution according to claim 2, wherein, the simulated body fluid components comprises a combination of one or two or more of $Na^+$, $K^+$, $Mg^{2+}$, $Ca^{2+}$, $Cl^-$, $HCO_3^-$, $HPO_4^{2-}$, $SO_4^{2-}$, $CO_3^{2-}$, $PO_4^{3-}$, $H_2PO_4^-$.

4. The method for preparing a bionic collagen aqueous solution according to claim 3, wherein, the acidic solution in step (1) and step (3) is at least one of hydrochloric acid, nitric acid, sulfuric acid, phosphoric acid, tartaric acid, citric acid, oxalic acid, acetic acid, and formic acid; the alkaline solution in step (3) comprises at least one of triethylamine, tetramethyl ethylenediamine, pyridine, piperidine, sodium hydroxide, potassium hydroxide, calcium hydroxide, magnesium hydroxide, ammonia, disodium hydrogen phosphate, and sodium bicarbonate; the concentration of the acidic solution or the alkaline solution is greater than or equal to 0.01 M and less than 10 M.

5. The method for preparing a bionic collagen aqueous solution according to claim 4, wherein, the connecting molecules are a mixture of one or two or more of isothiocyanate, isocyanate, acyl azide, N-hydroxysuccinimide ester, sulfonyl chloride, aldehyde, epoxide, aryl halide, imide ester, carbodiimide, acid anhydride, fluorophenyl ester, procyanidine, and genipina, and the connecting molecules in the bionic collagen aqueous solution has a final concentration of greater than or equal to 0.0001 wt. % of and less than or equal to 10 wt. %.

6. The method for preparing a bionic collagen aqueous solution according to claim 5, wherein, the final concentration of the connecting molecules in the bionic collagen aqueous solution is greater than or equal to 0.0001 wt. % of and less than or equal to 1 wt. %.

7. The method for preparing a bionic collagen aqueous solution according to claim 6, wherein, the final concentration of the connecting molecules in the bionic collagen aqueous solution is greater than or equal to 0.0001 wt. % of and less than or equal to 0.1 wt. %.

8. The method for preparing a bionic collagen aqueous solution according to claim 7, wherein, the final concentration of the connecting molecules in the bionic collagen aqueous solution is greater than or equal to 0.001 wt. % of and less than or equal to 0.01 wt. %.

9. The method of using a bionic collagen aqueous solution according to claim 8, wherein, the bionic collagen aqueous solution is used to cover the surface of a pre-repaired wound in a form of a dressing or applied to the body in an injected manner within 30 min after its preparation.

\* \* \* \* \*